United States Patent
Hendriks et al.

(10) Patent No.: US 9,107,694 B2
(45) Date of Patent: Aug. 18, 2015

(54) EXAMINATION APPARATUS

(75) Inventors: Bernardus Hendrikus Wilhelmus Hendriks, Eindhoven (NL); Adrien Emmanuel Desjardins, Eindhoven (NL); Martin Franciscus McKinney, Minneapolis, MN (US)

(73) Assignee: Koninklijke Philips N.V., Eindhoven (NL)

( * ) Notice: Subject to any disclaimer, the term of this patent is extended or adjusted under 35 U.S.C. 154(b) by 621 days.

(21) Appl. No.: 13/146,223

(22) PCT Filed: Jan. 25, 2010

(86) PCT No.: PCT/IB2010/050308
§ 371 (c)(1),
(2), (4) Date: Jul. 27, 2011

(87) PCT Pub. No.: WO2010/086778
PCT Pub. Date: Aug. 5, 2010

(65) Prior Publication Data
US 2012/0020459 A1 Jan. 26, 2012

(30) Foreign Application Priority Data
Jan. 30, 2009 (EP) .................................... 09151687

(51) Int. Cl.
*G01N 23/04* (2006.01)
*H05G 1/08* (2006.01)
(Continued)

(52) U.S. Cl.
CPC ............... *A61B 17/3403* (2013.01); *A61B 6/12* (2013.01); *A61B 6/463* (2013.01); *A61B 6/464* (2013.01);
(Continued)

(58) Field of Classification Search
CPC ..................... A61B 17/3403; A61B 2019/507; A61B 19/5244; A61B 19/5225; A61B 5/06; A61B 6/464; A61B 8/42; A61B 8/4245
USPC .......................... 378/62, 98.12; 600/407, 424
See application file for complete search history.

(56) References Cited

U.S. PATENT DOCUMENTS

| 4,246,607 | A |   | 1/1981 | Vijverberg |
| 5,038,786 | A | * | 8/1991 | Kojima ......................... 600/410 |
| 5,732,703 | A | * | 3/1998 | Kalfas et al. .................. 600/407 |
| 5,748,767 | A | * | 5/1998 | Raab ............................. 382/128 |
| 6,041,249 | A | * | 3/2000 | Regn ............................. 600/429 |

(Continued)

FOREIGN PATENT DOCUMENTS

| EP | 1551178 | 7/2005 |
| JP | H0492642 A | 8/1990 |

(Continued)

*Primary Examiner* — David J Makiya
*Assistant Examiner* — Dani Fox

(57) ABSTRACT

The present invention relates to an examination apparatus for providing information about an object and a method for providing information about an object of interest. In order to improve the visual reception of information relating to the object, an examination apparatus is provided that comprises an examination arrangement and a control unit with at least a first interface and a second interface. The examination arrangement is adapted to detect object data from at least one region of interest of an object and to provide the object data to the control unit. Further, the control unit is adapted to compute object data into object information and to transform at least a part of the object information into image data (32, 36). Further, the control unit is arranged to extract pre-determined indicative data from the object information and to transform the indicative data into graphical advisory data (40). The first interface is configured such to provide the image data to a display unit (20) in order to display the image data (32, 36) to the user. The second interface is configured such to provide a signal for an ambient advice display arrangement in order to provide the graphical advisory data (40) to the user.

13 Claims, 7 Drawing Sheets

(51) Int. Cl.
  *A61B 17/34* (2006.01)
  *A61B 6/12* (2006.01)
  *A61B 6/00* (2006.01)
  *G06F 19/00* (2011.01)
  *H05B 33/08* (2006.01)
  *A61B 19/00* (2006.01)
  *A61B 17/00* (2006.01)

(52) U.S. Cl.
  CPC ............... *A61B 6/467* (2013.01); *A61B 19/56* (2013.01); *G06F 19/321* (2013.01); *H05B 33/0803* (2013.01); *A61B 19/5202* (2013.01); *A61B 2017/00035* (2013.01); *A61B 2017/00061* (2013.01); *A61B 2017/00084* (2013.01); *A61B 2017/00128* (2013.01); *A61B 2019/507* (2013.01); *A61B 2019/5229* (2013.01); *A61B 2019/5238* (2013.01); *A61B 2019/564* (2013.01)

(56) References Cited

U.S. PATENT DOCUMENTS

| | | | |
|---|---|---|---|
| 6,366,796 B1 * | 4/2002 | Yanof et al. | 600/407 |
| 7,383,076 B2 | 6/2008 | Ntziachristos et al. | |
| 2003/0028091 A1 * | 2/2003 | Simon et al. | 600/407 |
| 2004/0034297 A1 * | 2/2004 | Darrow et al. | 600/407 |
| 2004/0097805 A1 * | 5/2004 | Verard et al. | 600/428 |
| 2005/0228246 A1 | 10/2005 | Lee et al. | |
| 2008/0297591 A1 * | 12/2008 | Aarts et al. | 348/51 |

FOREIGN PATENT DOCUMENTS

| | | |
|---|---|---|
| JP | H11161813 A | 12/1997 |
| JP | 2005300359 A | 10/2005 |
| JP | 2007128212 A | 5/2007 |
| WO | WO2007113737 | 10/2007 |
| WO | WO2008007293 | 1/2008 |
| WO | 2008081387 A1 | 7/2008 |

* cited by examiner

EXAMINATION APPARATUS

FIELD OF THE INVENTION

The present invention is related to an examination apparatus for providing information about an object and a method for providing information about an object of interest.

BACKGROUND OF THE INVENTION

Information about an object can be required, for example, during an intervention to provide necessary or desired knowledge of the object in order to be able to perform further interventional steps. This knowledge can serve as a sort of feedback, for example in cases where the results of the intervention are difficult to detect, such as in cases where the object of interest is a patient, where medical intervention can be performed in such a way that the actual interventional process or even the result cannot be detected by the person performing the intervention. It is therefore known for example, to provide display screens or monitors during interventions, such as surgical interventions, where information about the state of a target area is shown in still images or even in real time moving images. For example, the data these images are based upon can be derived by the means of X-rays, MRI, Ultrasound, SPECT etc. Especially in minimally invasive procedures, the surgeon is thus provided with the information necessary for performing the intervention. For fast and accurate localizing a monitor displaying an X-ray image in addition with a partial image provided by a television camera of the site to be targeted by X-ray radiation is described in U.S. Pat. No. 4,246,607.

SUMMARY OF THE INVENTION

But it has shown that due to an increasing number of parameters that can be displayed to provide information about the object of interest, for example the patient, the user sometimes experiences a fatigue that leads to a decrease in the user's performance and concentration during the intervention.

There may exist a need to improve the visual reception of information relating to the object.

The object is reached with an examination apparatus and a method, according to the independent claims.

In an exemplary embodiment, the examination apparatus for providing information about an object comprises an examination arrangement and a control unit with at least a first interface and a second interface. The examination arrangement is adapted to detect object data from at least one region of interest of an object and to provide the object data to the control unit. Further, the control unit is adapted to compute object data into object information and to transform at least a part of the object information into image data. Further, the control unit is arranged to extract pre-determined indicative data from the object information and to transform the indicative data into graphical advisory data. The first interface is configured such to provide the image data to a display unit in order to display the image data to the user. The second interface is configured such to provide a signal for an ambient advice display arrangement in order to provide the graphical advisory data to the user.

One of the advantages of the invention is that additional information in form of the indicative data, respectively the graphical advisory data, can be provided to the user without the means of a display unit. In other words, the image data containing, for example, conventional information about the object, is not affected by the provision of the graphical advisory data. By providing the graphical advisory data in the ambience of the examination apparatus the user can concentrate on the data provided on the display unit so that the reception of the content displayed on the display unit is not interfered by the provision of the advisory data. This is because the advisory data can be perceived by the user in a way which does not lead to fatigue or a decrease in concentration.

Of course, the appearance of the advisory information shown by the ambient advice display arrangement should be coded depending on the medical imaging methods and according to the type of intervention to ensure a widespread use of the invention and to allow an easy perception of the information communicated to the user. For example, the selection of the type of advisory data and its coded colors or brightness or patterns for the ambient advice display arrangement should be performed depending on the physicians' needs.

The ambient advice display arrangement can be defined as a secondary display arrangement. But it is noted that the wording 'secondary' does not refer to an actual number of displays but rather to the character of the information shown on the display and the ambient advice display arrangement.

Since the ambient light provided by the ambient advice display arrangement does not depend on the actual image shown on the display unit but rather on the object data derived by the examination arrangement, the provision of graphical advisory data to the user by the ambient advice display arrangement has the effect that an interaction of the user can lead to a change of the ambient light controlled by the ambient advice display arrangement because the extraction of pre-determined indicative data from the object information is performed in real time, or at least in near real time, since the object data is also detected in real time, or near real time, by the examination arrangement. Further, in case the advisory data is related to a state or condition of certain parameters of a patient, a change of the ambient light may occur without an interaction by the user but in any case a relation between the image displayed on the display unit and the ambient light is not at hand.

In an exemplary embodiment the control of the ambient advice display arrangement is performed in real time to provide accurate information to the user.

Preferably the signal for the ambient advice display arrangement is only depending on the object information. In other words, the signal is independent from the image displayed on the display unit.

This provides the possibility to determine certain required data or parameters and to provide this information as indicative or advisory information to the user's visual senses. For example, for certain conditions of the patient, thresholds can be pre-determined and monitored by the examination arrangement. Once a parameter reaches a critical value, that means once a threshold is reached, the ambient advice display arrangement provides a respective graphical advisory data to the user.

In one exemplary embodiment, this signal can be a one-dimensional signal in order to vary the colour or the brightness of at least one light source of the ambient advice display arrangement. For example, once the parameter reaches a critical condition the colour of the light provided by the ambient advice display is changed so that the user can easily receive this information without the need to superimpose this information in form of values or parameter numbers on the image data displayed on a display unit which can lead to an information overload on the display unit.

Preferably, the image data constitutes the central area of visual perception for the user and the graphical advisory data is provided in at least a part of the peripheral sub-zone of a user's area of visual perception outside the central area of visual perception.

One of the advantages of this embodiment is that the user can view the image data focusing on the content displayed on the display unit. Thus, the user can fully concentrate on the information shown on the display. But the present invention also uses the potential perception or cognition that is so far unused. In the peripheral sub-zone of the user's area of view it is, for example, usually not possible to read or detect numbers or values but it is still possible to detect changes of brightness or colour or patterns in this peripheral part of the field of view. Hence, the graphical advisory data preferably comprises information or aspects that can be communicated to the user by rather simple visual effects, for example a change of colour or change of brightness representing determined data. In other words, the graphical advisory data is displayed in a rather simple way compared to the content of the image shown by the display unit.

In an exemplary embodiment, a user interface to input data is provided in order to allow a determination of the kind of indicative data according to the user's needs.

In an exemplary embodiment of the invention, the examination apparatus comprises a display unit to display the image data and an ambient advice display arrangement to provide the graphical advisory data to the user.

Thus, an examination apparatus is provided that enhances the communication of the data to the user necessary, for example for a surgical intervention.

The graphical advisory data is provided outside the display area of display unit in order not to interfere with the information provided by the display unit.

Thus, the image data that constitutes a central area of visual perception for the user can be perceived by the user focusing on the display unit, whereas the graphical advisory data that is provided in at least a part of the peripheral sub-zone of the user's area of visual perception, in other words, that is provided outside the central area of visual perception, can also be perceived and thus communicated to the user.

Of course, the display unit can comprise one or more monitors or display screens. For example, reconstructional images of a region of interest of a patient can be shown on one monitor and certain parameters defining the condition of the patient can be displayed on an additional monitor arranged in the vicinity of the first monitor.

In a further exemplary embodiment, the examination arrangement comprises a first examination device arranged to provide morphological information.

This morphological information serves as basic information provided to the user.

Preferably, the examination arrangement comprises a second examination device arranged to provide molecular information.

For example, during a needle intervention the molecular information can inform the user about the molecular condition at the tip of the needle inserted by the user.

Further preferred is an exemplary embodiment where the second examination device provides data resulting from monitoring organic functions of the patient.

For example, colors can be used to inform the user about certain changes of an important organ of the patient.

In a preferred exemplary embodiment, the graphical advisory data is based on optical spectroscopic information.

For example, the spectroscopic information is derived with diffuse reflectance spectroscopy.

For further example, the spectroscopic information is obtained by Raman spectroscopy and/or (auto)fluorescence spectroscopy.

In another preferred embodiment, the graphical advisory data is based on data obtained by non-optical methods.

In an exemplary embodiment, the graphical advisory data is based on measuring temperature and/or pH to provide additional information to the morphology data.

For example, measuring temperature or pH can be useful to detect whether a site is reached where tissue is inflamed.

In a preferred embodiment, optical and non-optical methods are used in combination.

This enables to provide sophisticated information to the surgeon for example.

For example, during so-called needle interventions it is possible to make needles more intelligent by adding optical methods providing molecular information to physicians. Diffuse reflectance spectroscopy allows, for example, to achieve information about the scatterers and chromophores within the tissue. By providing this information to the user, the user is supported so that the process of making guidance decisions, which have to be made extremely quickly in order to avoid tissue damage, is relieved because the diffuse reflectance spectroscopy (DRS) information is presented in a concise and unobtrusive way that does not distract the physician too much from the original intervention since the spectroscopic information is displayed as an ambient information.

In an exemplary embodiment, the graphical advisory data comprises directional information.

For example, different colors could correspond to different distances between, for example, chromophores and the probe, that is the needle directed by the user. For example, a blue colour could correspond to large distances when the probe is far from the target tissue and a red colour could correspond to the case where the probe is within the target tissue.

In another embodiment, the directional information being displayed by changing the light of the ambient advice display arrangement as a function of the position of the needle or another interventional device directed by the user around the display unit or monitor. For instance, in the case that a targeted tissue is approached from the left side of the needle, yellow light is displayed on the left of the display unit while red light is displayed on the right side of the display unit.

In another exemplary embodiment, the ambient advice display arrangement comprises an illumination system with at least one light source arranged for adjustably illuminating a part of a surface area behind a display unit.

By illuminating a surface area behind the display unit it is ensured that the image data displayed on the display unit is not disturbed by superimposing information which would lead to an information overflow on the side of the user. When the user watches the display unit and focuses on the image data provided on the display unit, the illuminated part of the surface area behind the display unit appears to the user in the user's peripheral part of his field of view.

Preferably the illuminated surface area is at least partially larger than the display area of the display unit to ensure that the advisory information provided by the ambient advice display arrangement is in any case noticed by the user standing in front of the display unit regarding the display unit.

For example, in case one or more monitors are provided within an examination room of a hospital the illuminated surface area could be a wall of the room behind the hanging monitors.

In another exemplary embodiment, an additional surface can be arranged behind the monitors so that the monitors can be moved to a desired position within the room according to the user's needs. This additional element behind the monitors acting as the illuminated surface of the ambient advice display arrangement would ensure that the advisory information is always presented to the user.

In another exemplary embodiment, the display area of a display unit is at least partially surrounded by a frame element and the ambient advice display arrangement comprises at least one illuminating device, illuminating at least a part of the frame element.

This allows for the provision of the advisory information in cases where rather large screens are used or where the distance of the user to the display unit is rather small. The direct vicinity of the adjustably illuminated frame element ensures that the advisory information is always recognized by the user. But as the frame element is arranged beside the display unit, the context of the display unit is not disturbed by the additional advisory information.

In a further exemplary embodiment, the ambient advice display arrangement comprises at least one interface arranged to control at least a part of an ambient lighting system of an examination laboratory.

By controlling at least a part of the ambient lighting system, for example of the room itself, the communication of the advisory information to the user is enhanced because it is ensured that this information is always recognized by the user, even in those cases where the user's view is not focused on the display unit but focused on the patient himself. Regardless of the direction of the user's view, a change of colour or a change of brightness or pattern of a part of the ambient lighting system will always be recognized by the user.

Preferably, the examination apparatus comprises a part of the ambient lighting system for an examination laboratory. For example, light sources can be provided that illuminate the surrounding walls or ceiling surfaces of the laboratory. This can either be done by direct illumination or indirect illumination of those surfaces. Of course, it is also possible to provide other ambient lighting elements.

In a preferred embodiment, the examination arrangement comprises an imaging modality.

In a further preferred exemplary embodiment, the examination arrangement comprises an X-ray imaging system with an X-ray image acquisition device comprising a source of X-ray radiation and an X-ray image detection module located opposite the source of X-ray radiation and a table provided to receive an object to be examined. Further, an interface unit is arranged to input information by the user. A control unit is connected to both the detection module and the radiation source and the interface unit. The X-ray images are computed to generate image data to be displayed as guidance images on the display unit.

Hence, interventional guidance is provided with the X-ray images displayed on the display unit. For example, in case of DRS measurements, this required information can be displayed on the ambient advice display arrangement, for example by the ambient light around the display units illuminating a surface behind the display unit. Hence, the ambient light information can be perceived by physicians without distracting them from interpreting the conventional images such as the X-ray images.

In another exemplary embodiment, the examination arrangement comprises an acoustic imaging system using ultrasound waves to generate images to be displayed on the display unit.

In a further exemplary embodiment, the examination arrangement comprises an MRI arrangement.

In a further exemplary embodiment, the examination arrangement comprises a SPECT arrangement.

According to the invention, in an exemplary embodiment, the object is also reached with an intervention laboratory system with an examination apparatus according to one of the preceding embodiments and an ambient lighting system wherein the control unit is arranged to control at least a part of the ambient lighting system to display the graphical advisory data to the user.

In other words, the examination apparatus, as described above, is integrated into the technical environment of an intervention laboratory.

The term 'intervention laboratory system' also refers to other examination rooms or areas in hospitals or other places where medical practice is performed.

According to the invention, in an exemplary embodiment, the object is also reached with a method for providing information about an object of interest comprising the following steps: First, object data is detected from at least one region of interest of an object. The detected object data is computed into object information. At least a part of the object information is then transformed into image data. Also, pre-determined indicative data is extracted from the object information. The indicative data is transformed into practical advisory data. The image data is displayed constituting a central area of visual perception for the user. The graphical advisory data is provided in at least a part of the peripheral sub-zone of the user's area of visual perception outside the central area of visual perception.

For example, the image data is displayed by a display unit and the graphical advisory data is provided with an ambient advice display arrangement.

One of the advantages of the method, according to the invention, is that graphical advisory data can be provided to the user without disturbing the perception of the image data. This leads to an easier perception by the user which improves the user's performance, in particular in relation to the aspects of concentration and fatigue.

In an exemplary embodiment of the method, the depiction of object data comprises generating at least one X-ray image and the X-ray image is displayed on a display unit.

In addition to X-ray radiation, other methods of medical imaging can also be used such as imaging based upon the activity, sound, ultrasonic sound, magnetic resonance imaging (MRI), nuclear magnetic resonance (NMR) or thermography, for example.

The X-ray images or the images according to one of the mentioned imaging processes are able to provide detailed morphological information needed for all kinds of different interventions.

In a further exemplary embodiment of the method, the detection of object data comprises the step of performing diffuse reflectance spectroscopy to derive spectroscopic information.

For example, the indicative data corresponds to different chromophores.

This allows providing additional information to the user which is not shown on the image data displayed by the display unit but which is of crucial importance to the performance of the intervention by the user.

In a further exemplary embodiment the method comprises the steps of acquiring spectral intensities, analyzing the spectral analysis, comparing the components and determining whether certain parameters are met and finally determining the signal for the ambient advice display.

For example, the acquisition step is performed using the formula:

$$\{I(\lambda_1), I(\lambda_2), I(\lambda_3), \ldots, I(\lambda_N)\}$$

where $\lambda_1$ and $\lambda_N$ are the minimum and the maximum light wave lengths. The spectral analysis is performed using principle components analysis. Further, in the comparison step, the components are compared with looking up values in a table. This classification is performed to determine whether the target structure is reached or not. Within the determination step a controller sends a signal that determines for example the colour of the ambient advice display arrangement. Hence, the ambient advice display arrangement colour is changed. The steps are repeated according to the duration of the intervention.

Of course, also the brightness or even a certain pattern of light generated by the ambient advice display arrangement can be changed instead of just changing the colour.

In another exemplary embodiment of the present invention, a computer program element is provided that is characterized by being adapted to perform the method steps of the method, according to one of the preceding embodiments.

Preferably, the computer program element is adapted to control an ambient advice display arrangement in response to the indicative data.

The computer program element might therefore be stored on a computing unit, which might also be part of an embodiment of the present invention. This computing unit may be adapted to perform or induce the performing of the steps of the method described above. Moreover, it may be adapted to operate the components of the above-described system. The computing unit can be adapted to operate automatically and/or to execute the orders of a user.

This exemplary embodiment of the invention covers both a computer program that right from the beginning uses the invention and a computer program that by means of an update turns an existing program into a program that uses the invention.

Further on, the computer program element might be able to provide all necessary steps to fulfill the procedure of the method as described above.

According to a further exemplary embodiment of the present invention, a computer-readable medium is presented wherein the computer-readable medium has a computer program element stored on it which computer program element is described by the preceding section.

According to a further exemplary embodiment of the present invention, a medium for making a computer program element available for downloading is provided, which computer program element is arranged to perform the method according to one of the previously described embodiments of the invention.

These and other aspects of the invention will be apparent from the exemplary embodiments described hereinafter with reference to the drawings.

DETAILED DESCRIPTION OF EMBODIMENTS

Figure 1:
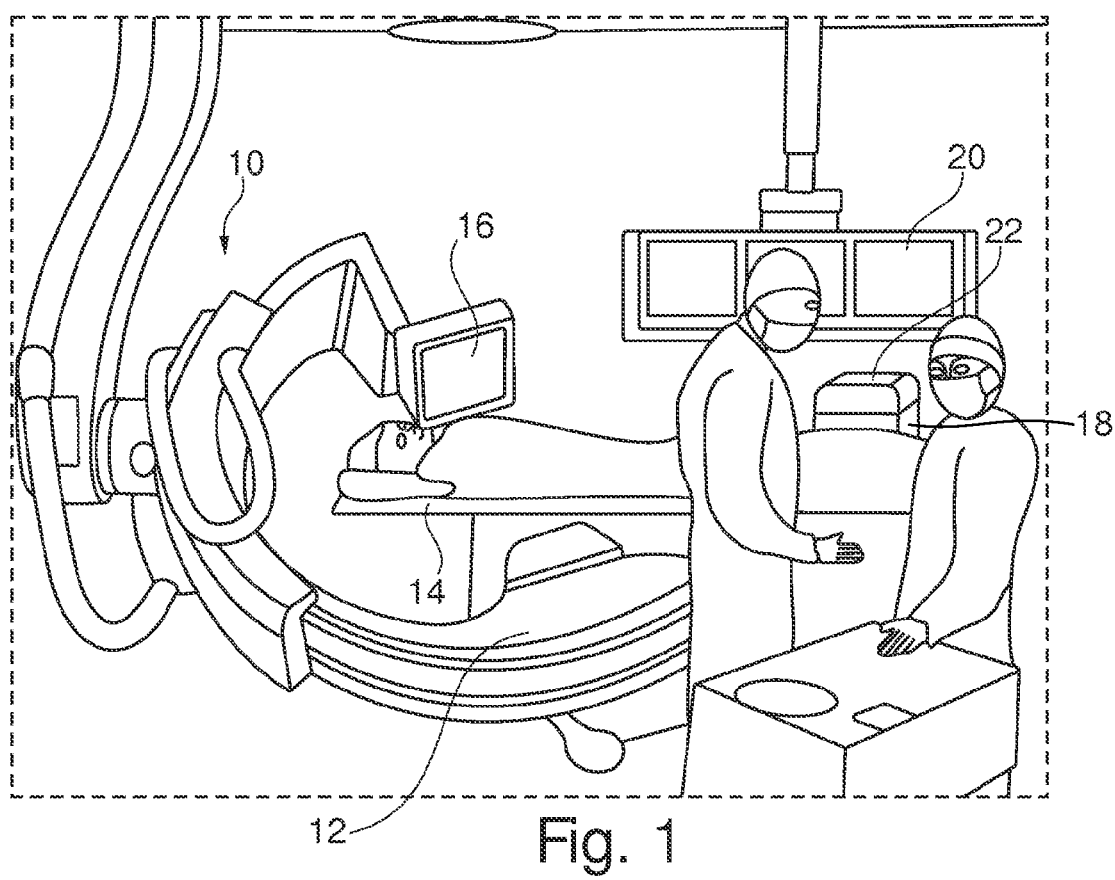
FIG. 1 schematically shows an example of an X-ray suite.

FIG. 1 schematically shows an X-ray suite with an examination apparatus comprising an X-ray imaging system 10 for the use in an intervention laboratory of a hospital, for example. The X-ray imaging system 10 comprises an X-ray image acquisition device with a source of X-ray radiation 12 provided to generate X-radiation. A table 14 is provided to receive a subject to be examined, for example a patient. Further, an X-ray detection module 16 is located opposite the source of X-ray radiation 12, i.e. during the radiation procedure, the subject is located between the source of X-ray radiation 12 and the detection module 16. The latter is sending data to a data processing unit or control unit 18, which is connected to both the detection module 16 and the radiation source 12. The calculation or control unit 18 is located in the vicinity of the table 14 or can also be located underneath the table 14 to save space within the laboratory. Of course, it could also be located at a different place, such as a different room. Furthermore, a display unit 20 is arranged in the vicinity of the table 14 to display information to the person performing the intervention. For example, a clinician such as a surgeon or physician. Preferably, the display unit 20 is moveably mounted to allow for individual adjustment depending on the examination situation. Also, an interface unit 22 is arranged to input information by the user. Basically, the image detection module 16 generates images by exposing the subject to X-ray radiation, wherein said images are further processed in the data processing unit or control unit 18. It is noted that the example shown is of a so-called C-type X-ray image acquisition device. Of course, the invention also relates to other types of X-ray acquisition devices. Further, it has also been noted that other medical imaging methods using different imaging technologies can also be used.

Further, the examination apparatus also comprises an examination arrangement which is adapted to detect object data from at least one region of interest of an object and to provide the object data to the control unit 18. For example, the examination arrangement comprises a first examination device in form of the X-ray imaging device and a second examination device (not shown) arranged to provide molecular information. For example, the second examination device comprises a biopsy needle containing optical fibers to allow for a diffuse reflectance spectroscopy (DRS) measurement.

By means of the X-ray image acquisition device, object data from a region of interest of a patient is detected and the object data is provided to control unit 18 where the object data is computed into object information. At least a part of the object information is transformed into image data. Further, pre-determined indicative data is extracted from the object information and transformed into graphical advisory data.

The control unit is provided with a first interface a second interface. A first interface is arranged for the connection of the display unit 20 in order to display the image data to the user. The second interface is arranged to connect an ambient advice display arrangement in order to provide a graphical advisory data to the user. The ambient advice display arrangement will be described in more detail below.

Figure 2:
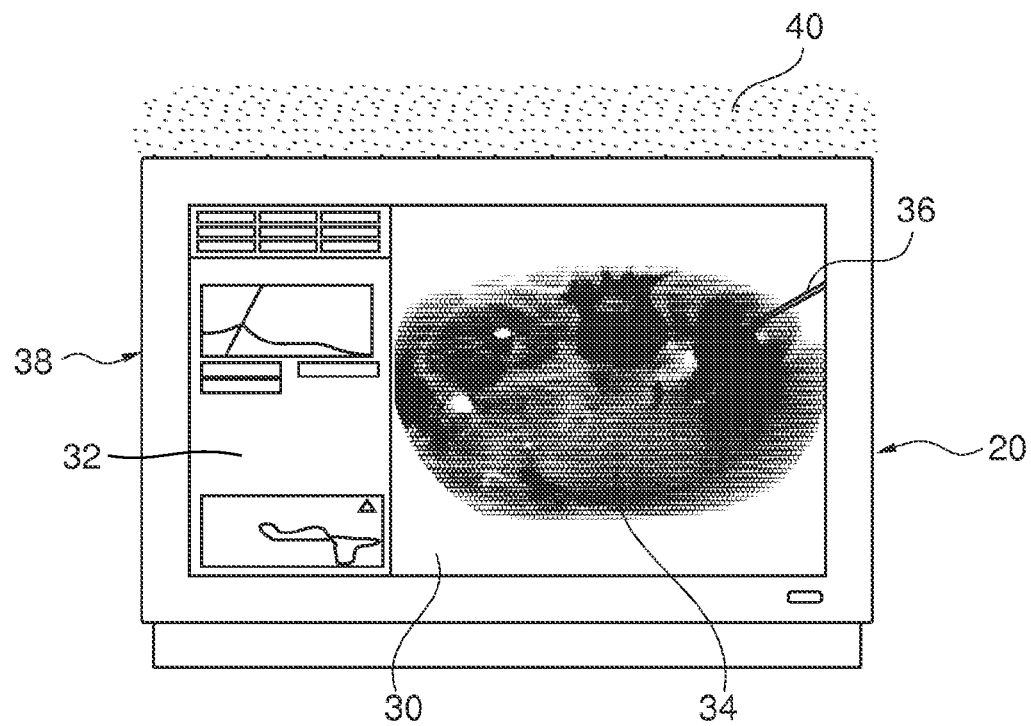
FIG. 2 schematically shows a display unit and an illuminated surface area behind the display unit illuminated by an ambient advice display arrangement, according to the invention.

In FIG. 2 a simplified embodiment of the display unit 20 is shown. Please note that the display unit 20 in FIG. 1 comprises several monitors whereas for the sake of clearance in FIG. 2 the display unit 20 only comprises one monitor. The display unit 20 displays image data to the user. Therefore, the display unit comprises a display area 30 that is subdivided into several areas according to different types of information shown to the user. For example, in the left part of the display area 30, a frame or window 32 is shown relating to several parameters defining certain aspects of the patient. This part of the display area also serves as an interface allowing inputting or changing or performing certain commands, depending on the user's needs. In the central and right part of the display area 30 an image or image sequence is shown providing morphological information to the user. In the right part of the image 34 the biopsy needle 36 can be seen which is controlled or directed by the user. Of course, the term 'user' also comprises not only one but also several persons operating the examination apparatus, according to the invention.

In order to provide the user with additional information without distracting from the information shown in the display area 30 an ambient advice display arrangement in form of an illumination system 38 with one or more light sources is arranged for adjustably illuminating a part of the surface area behind the display unit 20 is provided.

Figure 3:
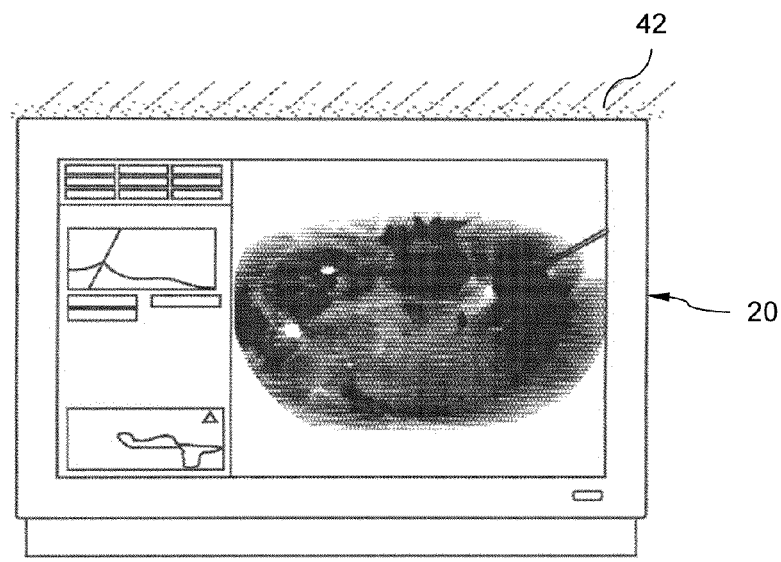
FIG. 3 shows the display of FIG. 2, wherein the ambient advice display arrangement presents a different graphical advisory information.

In the exemplary embodiment shown in FIG. 2, the ambient advice display arrangement is hidden behind the display unit 20. As an example, the biopsy needle 36 provides molecular information. This can be used to determine whether the needle has reached the targeted site or not. While the user is watching or focusing on the content shown on the display unit 20, the information about the position of the needle is not provided within the image data shown in the display unit 20 but provided by the ambient advice display arrangement. When the needle 36 has not reached the targeted site, the ambient lighting is blue, which is indicated in FIG. 2 by a dot-like pattern 40 around the display unit 20. When the needle has reached the targeted site the lighting becomes red, which is indicated in FIG. 3 by a dotted-line pattern 42.

It is to be noted that the ambient light can also be displayed in certain parts around the display relating to certain aspects in order to provide more than one advisory data aspect.

Hence, the ambient light information is serving as advisory information that can be perceived by physicians without distracting them from interpreting conventional images such as the X-ray image shown in the display unit 20.

Figure 4:
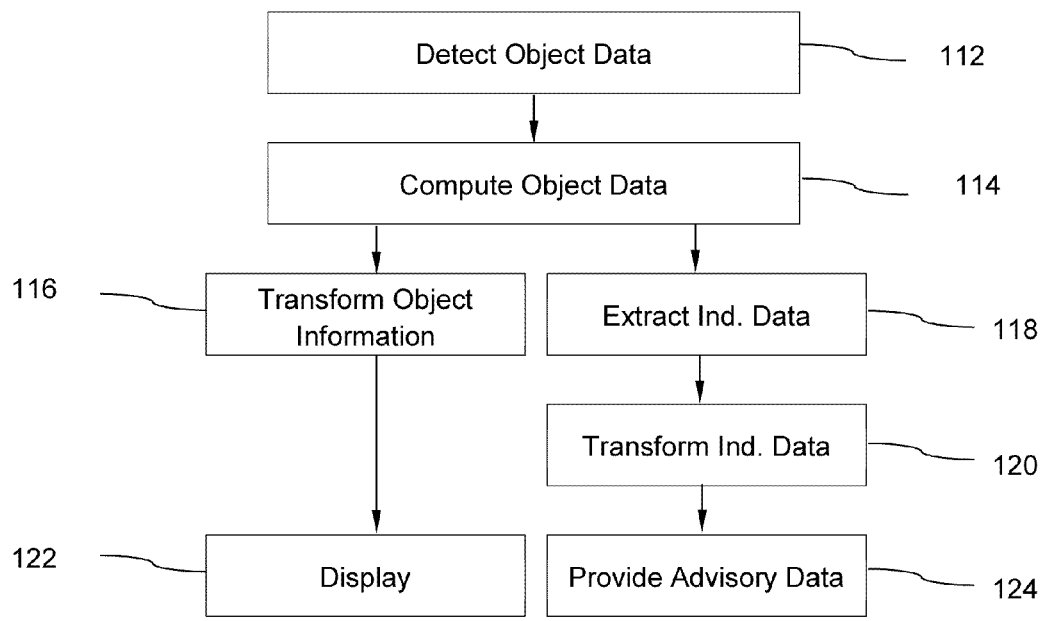
FIG. 4 shows the basic steps of an exemplary embodiment of the method to control the ambient advice display arrangement.

FIG. 4 shows the basic steps according to the invention to provide information about an object of interest to the user. First, object data is detected 112 from at least one region of interest of an object. The detected object data is computed 114 into object information. At least a part of the object information is then transformed 116 into image data. Also, pre-determined indicative data is extracted 118 from the object information. The indicative data is transformed 120 into practical advisory data. The image data is displayed 122 constituting a central area of visual perception for the user. The graphical advisory data is provided 124 in at least a part of the peripheral sub-zone of the user's area of visual perception outside the central area of visual perception.

Figure 5:
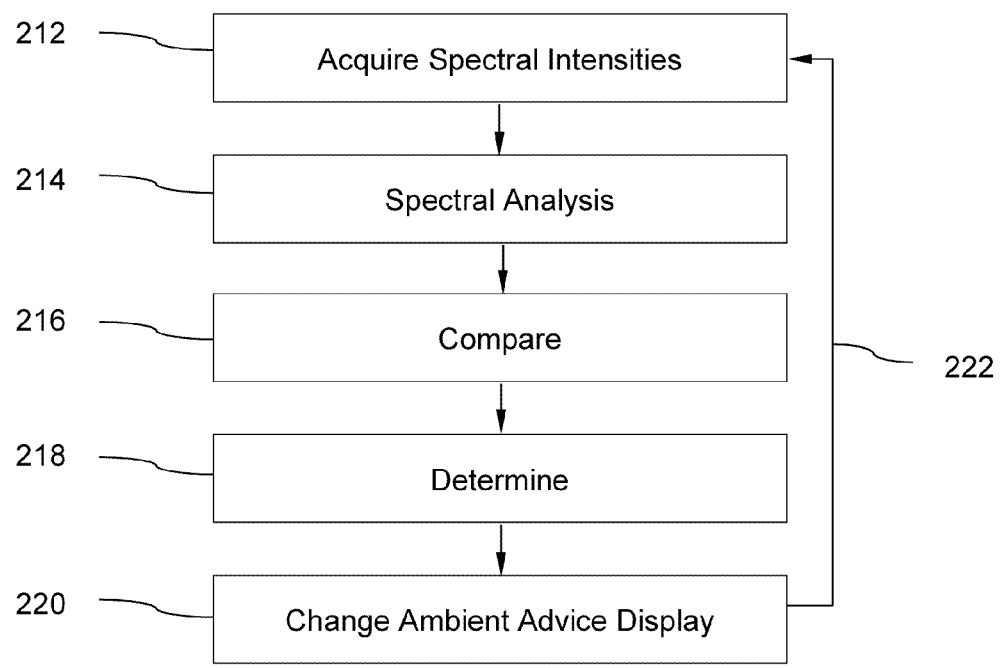
FIG. 5 shows an algorithm for addressing an ambient advice display arrangement, according to the invention.

In FIG. 5 the principle algorithm for addressing the ambient advice display arrangement is shown. First, in an acquisition step 212 spectral intensities are required:

$$\{I(\lambda_1), I(\lambda_2), I(\lambda_3), \ldots, I(\lambda_N)\}$$

where $\lambda_1$ and $\lambda_N$ are the minimum and the maximum light wave lengths, respectively.

Then in an analysis step 214, the spectral analysis is performed using principle components analysis. Further, in a comparison step 216, the components are compared with looking up values in a table. This classification is performed to determine whether the target structure is reached or not.

Then in a determination step 218, a controller sends a signal that determines the colour of the ambient advice display arrangement. Then the ambient advice display arrangement colour is changed 220. Of course, also the brightness or even a certain pattern of light generated by the ambient advice display arrangement can be changed instead of just changing the colour. These steps are repeated 222 according to the duration of the intervention. It has to be noted that the control of the ambient advice display arrangement is performed in real time to provide accurate information to the user.

Figure 6:
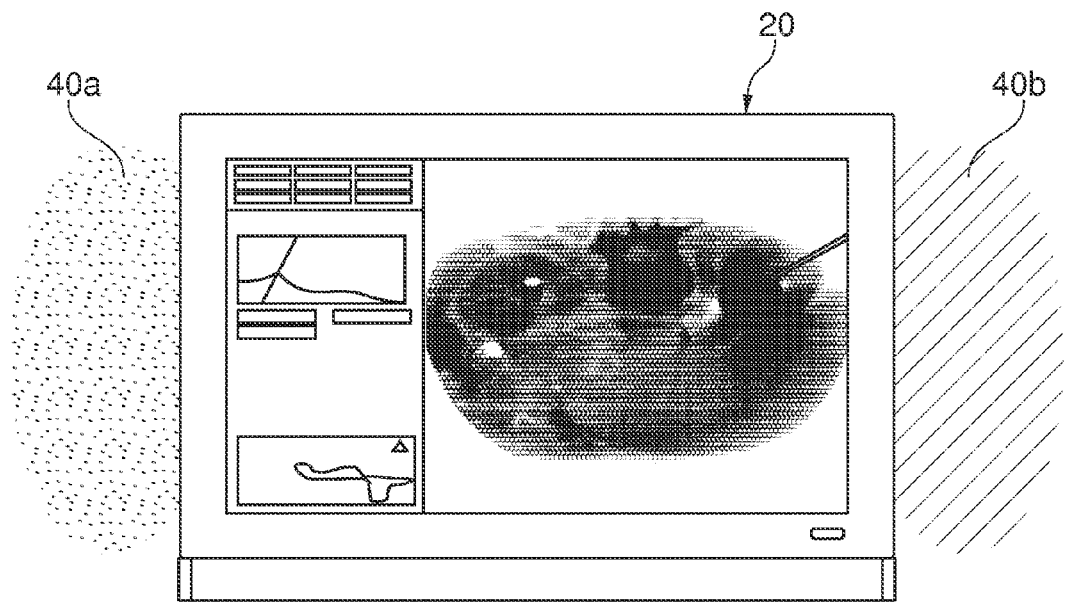
FIG. 6 shows a further example of FIGS. 2 and 3.

The visual information provided by the ambient advice display arrangement can also be structured according to the orientation information acquired from a photonic needle, for example. For instance, in the case shown in FIG. 6 the structure or area of the patient to be reached by the needle is at the left of the needle. As advisory information, yellow light is displayed on the left side of the monitor while blue light is displayed on the right side of the monitor, which is indicated in FIG. 6 by two different patterns 40a and 40b.

Of course, these examples of the possible advisory information are rather simple for the sake of simplicity. It is to be noted that more complex information can be provided to the user. However, the ambient advice display arrangement is depending on the perception of possibility of the user which is rather limited in the peripheral area of the field of view compared with a central area of the field of view. But nevertheless, the peripheral part of the field of view still provides for a great potential of advisory information which leads to a relief or improvement in respect to the reception of the information displayed by the display unit 20.

Figure 7:
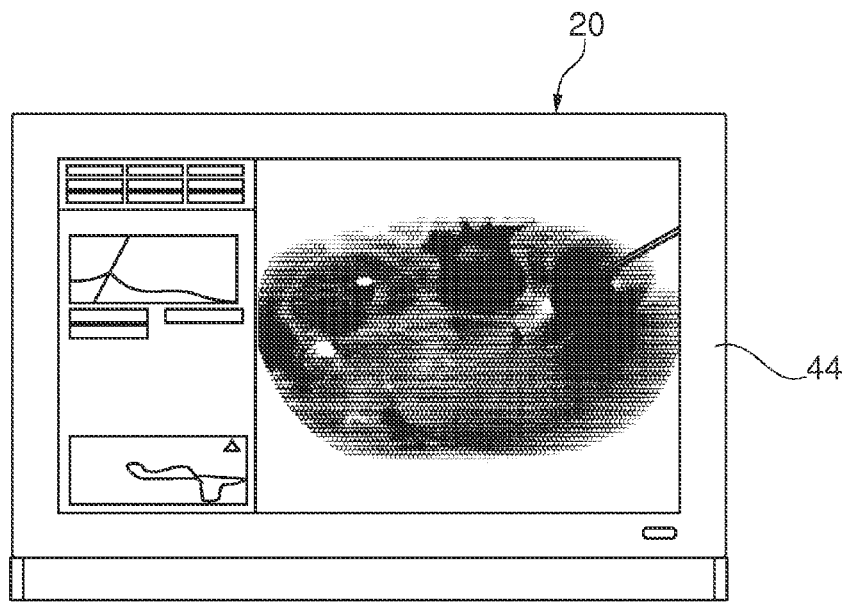
FIG. 7 schematically shows a display unit with an illuminated frame surrounding the display area as an ambient advice display arrangement.

In another exemplary embodiment shown in FIG. 7 the display area 30 of the display unit 20 is surrounded by a frame element 44 and the ambient advice display arrangement comprises an illuminating device (not shown in FIG. 7) illuminating at least a part of the frame element. For example, light sources are arranged behind the frame element 44 which is translucent itself Without illumination, the frame appears in a neutral way. When operating the examination apparatus, the ambient advice display arrangement controls the light sources such that the frame itself appears in different colors having a different brightness depending on the type of information provided to the user.

Of course, the appearance of the advisory information shown by the ambient advice display arrangement should be coded depending on the medical imaging methods and according to the type of intervention to ensure a widespread use of the invention and to allow an easy perception of the information communicated to the user. For example, the selection of the type of advisory data and its coded colors or brightness or pattern of the ambient advice display arrangement should be performed depending on the physician's needs.

The illuminated frame can be used in addition to or even instead of illuminating a surface area behind the display unit 20.

Figure 8:
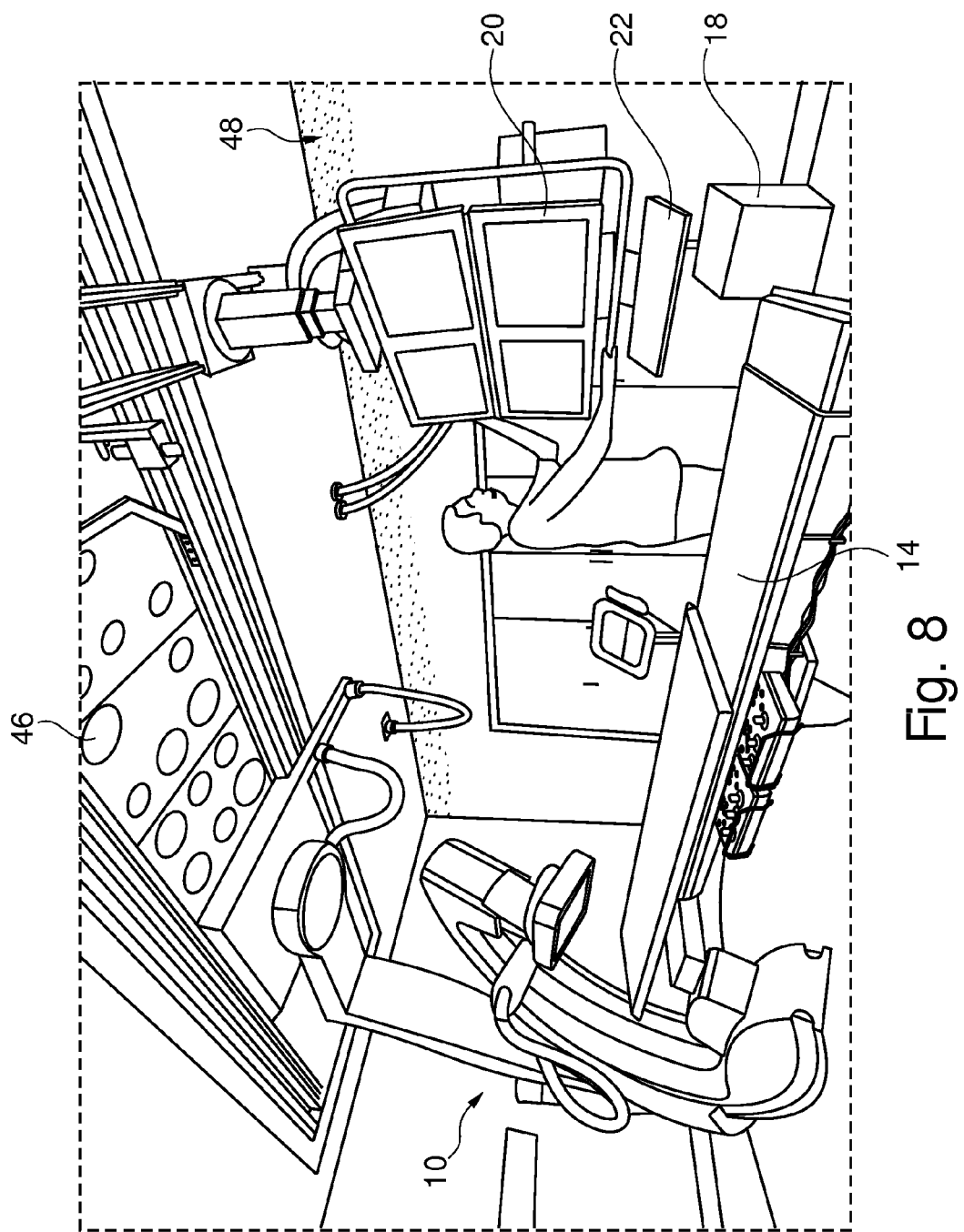
FIG. 8 shows a further example of an X-ray suite.
Figure 9:
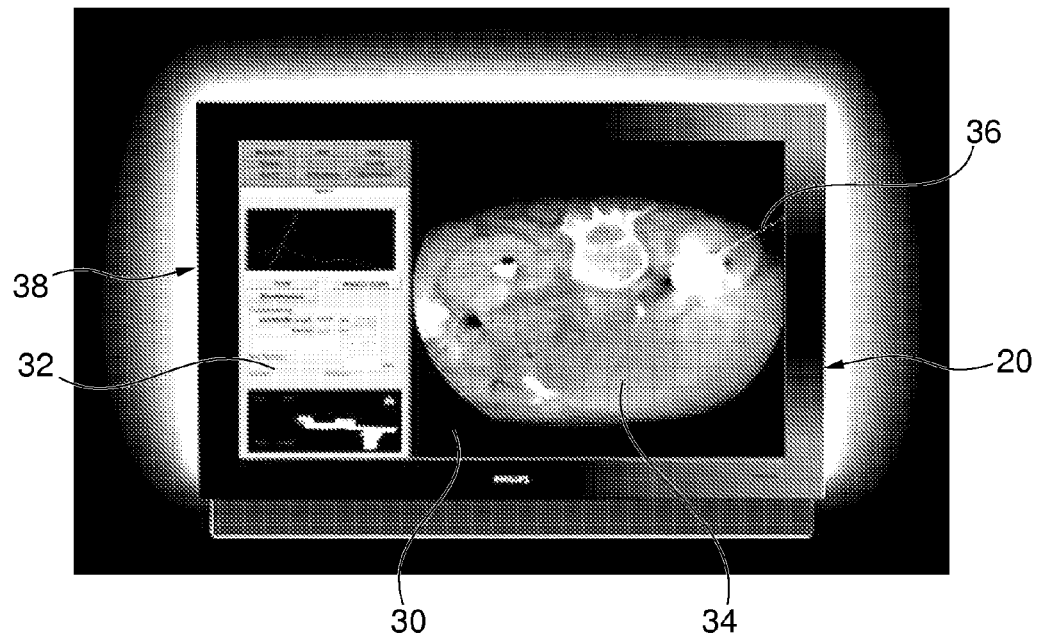
FIG. 9 shows an image of FIG. 2.
Figure 10:
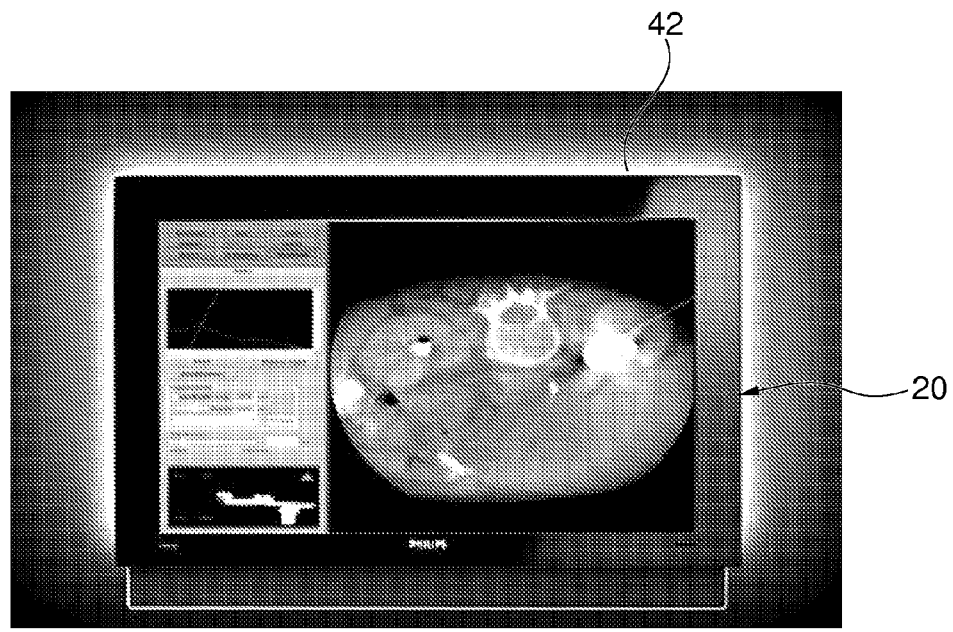
FIG. 10 shows an image of FIG. 3.
Figure 11:
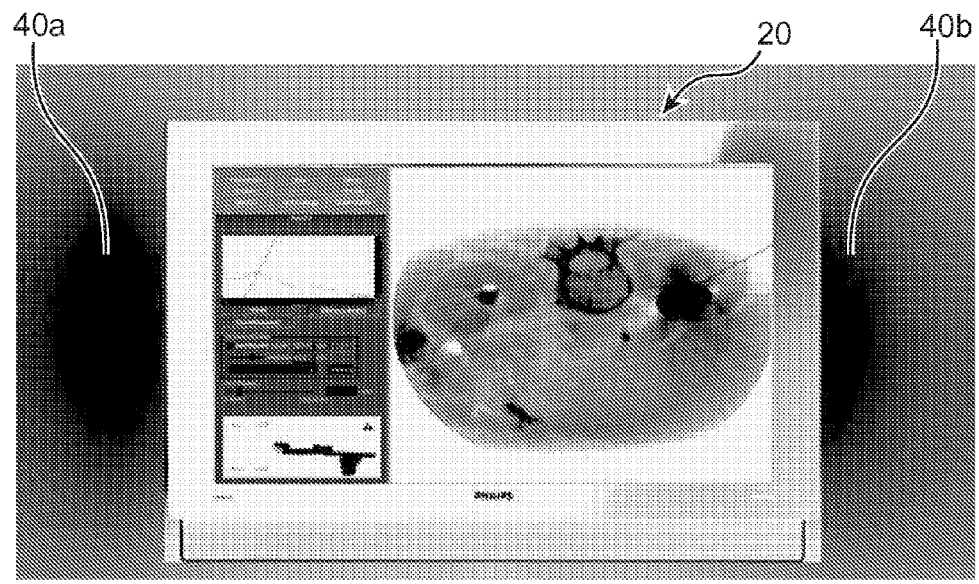
FIG. 11 shows an image of FIG. 6.
Figure 12:
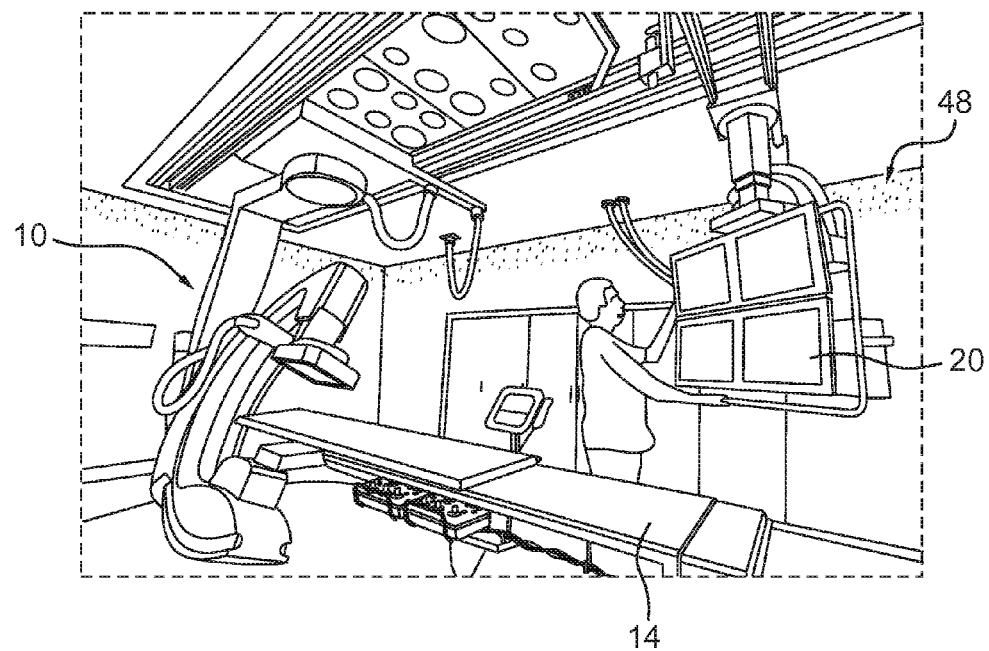
FIG. 12 shows an image of FIG. 8.

In another embodiment shown in FIG. 8 the ambient advice display arrangement controls at least a part of the lighting system within the operating or imaging suite. In the example shown in FIG. 8, the lighting system comprises, for example, ceiling lights 46 and ambient lights 48. This so-called structured lighting provides the possibility that not the complete operating room has to change its colour that is the colour of the light, but for instance only a part of a wall by controlling only the ambient light 48. For example, the wall behind the display unit 20 can be illuminated as well as the opposing wall not shown in FIG. 8. This allows for communication of the advisory information to the user even in those cases where the user's view is not focused on the display unit 20 but focused in another direction, for example on the patient.

However, independent of the actual chosen embodiment, the ambient advice display arrangement provides visually detectable changes that can easily be interpreted by the user as certain types of advisory information. It is to be noted that the visual changes appear in accordance to the detected object data and not in direct relation to the image content shown on the display unit. In other words, according to the invention, the image data shown on the display 20 can stay the same, or nearly the same, whereas the ambient light provided by the ambient advice display arrangement changes, for example, by a change of colour, brightness or the light pattern itself provided by the ambient advice display arrangement, due to a movement or steering of the needle performed by the user. Of course, it is also possible that the image data shown on the display unit 20 changes due to monitoring different parameters or aspects that are shown one behind the other, whereas the ambient light stays the same, for example when the needle is not moved by the operator in cases where the ambient light serves as directional information for the steering of a biopsy needle.

In addition to the drawings in FIGS. 2, 3, 6 and 8, photographs are shown in FIGS. 9, 10, 11 and 12.

While the invention has been illustrated and described in details in the drawings and forgoing description, such illustration and description are to be considered illustrative or exemplary and not restrictive; the invention is not limited to the disclosed embodiments.

The invention claimed is:

1. An examination apparatus for providing information about an object, comprising
   an examination arrangement; and
   a control unit (18) with at least a first interface and a second interface;
   wherein the examination arrangement is adapted to detect object data from at least one region of interest of an object and to provide the object data to the control unit (18);
   wherein the control unit (18) is adapted to compute the object data into object information and to transform at least a part of the object information into image data (32, 36); and wherein the control unit (18) is further arranged to extract predetermined indicative data from the object information and to transform the indicative data into graphical advisory data (40); and
   wherein the first interface is configured such to provide the image data to a display unit (20) in order to display the image data to the user; and
   wherein the second interface is configured such to provide a signal for an ambient advice display arrangement in order to provide the graphical advisory data to the user:
   the examination arrangement further comprising a display unit (20) to display the image data; and an ambient advice display arrangement to provide the graphical advisory data to the user.

2. The examination apparatus according to claim 1, where the examination arrangement comprises a first examination device arranged to provide morphological information.

3. The examination apparatus according to claim 1, wherein the graphical advisory data is based on optical spectroscopic information.

4. The examination apparatus according to claim 1, where the graphical advisory data comprises directional information.

5. The examination apparatus according to claim 1, where the ambient advice display arrangement comprises an illumination system with at least one light source arranged for adjustably illuminating a part of a surface area behind the display unit (20).

6. The examination apparatus according to claim 1, where the display area of the display unit (20) is at least partially surrounded by a frame element (44) and wherein the ambient advice display arrangement comprises at least one illuminating device illuminating at least a part of the frame element displayed (44).

7. The examination apparatus according to claim 1, where the ambient advice display arrangement (48) comprises at least one interface arranged to control at least a part of an ambient lighting system of an examination laboratory.

8. The examination apparatus according to claim 1, where the examination arrangement comprises an X-ray imaging system (10) with an X-ray image acquisition device comprising a source of X-ray radiation (12) and an X-ray image detection module (16) located opposite the source of X-ray radiation and a table (14) provided to receive an object to be examined, and an interface unit (22) arranged to input information by the user; wherein the control unit (18) is connected to both the detection module (16) and the radiation source (12) and to the interface unit (22); and wherein the X-ray images are computed to generate image data to be displayed as guidance images on the display unit (20).

9. An intervention laboratory system with an examination apparatus according to claim 1 and an ambient lighting system (48), wherein the control unit (18) is arranged to control at least a part of the ambient lighting system to display the graphical advisory data to the user.

10. A method for providing information about an object of interest, comprising the following steps:
    detecting (112) object data from at least one region of interest of an object;
    computing (114) the detected object data into object information;
    transforming (116) at least a part of the object information into image data;
    extracting (118) predetermined indicative data from the object information;
    transforming (120) the indicative data into graphical advisory data;
    displaying (122) the image data constituting a central area of visual perception for the user; and
    providing (124) the graphical advisory data in at least a part of the peripheral subzone of the user's area of visual perception outside the central area of visual perception.

11. The method according to claim 10, where the detection of object data comprises generating at least one X-ray image and where the X-ray image is displayed on a display unit.

12. The method according to claim 10, where the detection of the object data comprises the step of performing diffuse reflectance spectroscopy to derive spectroscopic information.

13. Computer readable storage device having stored thereon a program of instruction, comprising:
    program instructions for detecting (112) object data from at least one region of interest of an object;
    program instructions for computing (114) the detected object data into object information;

program instructions for transforming (116) at least a part of the object information into image data;

program instructions for extracting (118) predetermined indicative data from the object information;

program instructions for transforming (120) the indicative data into graphical advisory data;

program instructions for displaying (122) the image data constituting a central area of visual perception for the user; and program instructions for providing (124) the graphical advisory data in an ambient advice display arrangement in at least a part of the peripheral subzone of the user's area of visual perception outside the central area of visual perception.

\* \* \* \* \*